United States Patent [19]

DiPerna et al.

[11] Patent Number: 5,685,836

[45] Date of Patent: Nov. 11, 1997

[54] CONTINUOUS CURVE YANKAUER

[75] Inventors: Paul M. DiPerna, Long Grove; Stephen R. Spehalski, Gurnee, both of Ill.

[73] Assignee: Allegiance Corporation, McGaw Park, Ill.

[21] Appl. No.: 475,952

[22] Filed: Jun. 7, 1995

[51] Int. Cl.$^6$ .................................................. A61M 1/00
[52] U.S. Cl. ............................................ 604/19; 604/240
[58] Field of Search ......................... 604/19, 27, 35, 604/36, 43, 49, 53, 264, 280

[56] References Cited

U.S. PATENT DOCUMENTS

| 1,366,320 | 1/1921 | Hufschmidt | 604/41 |
| 1,581,508 | 4/1926 | Bomhord | 604/41 |
| 3,752,617 | 8/1973 | Burlis et al. | |
| 5,387,199 | 2/1995 | Siman et al. | |
| 5,411,472 | 5/1995 | Steg, Jr. et al. | |

*Primary Examiner*—Manuel Mendez
*Attorney, Agent, or Firm*—Robert A. Stenzel; John G. Premo

[57] ABSTRACT

The invention provides an improved yankauer used to aspirate body fluids during surgical procedures. It comprises a conventional hollow tip the back end of which is connected to flexible tubing which transports the aspirated body fluids. The section of the yankauer behind the hollow tip is a curved arm having a channel extending throughout its length which receives the flexible tubing. The other end of the curved arm is connected to a handle which also contains a channel which receivs the flexible tubing. In a preferred embodiment of the invention the channels in the curved arm and the handle are troughs.

10 Claims, 2 Drawing Sheets

CONTINUOUS CURVE YANKAUER

FIELD OF THE INVENTION

The invention relates to improved yankauers used to aspirate surgical fluids.

BACKGROUND OF THE INVENTION

Yankauers are curved aspirating wands used during surgical procedures to aspirate body fluids such as blood. Conventional yankauers are constructed to have a body fluid removing tip the head portion of which is at least partially open to contact the body fluids. The most common configuration of the tip is ball shaped. The ball is hollow and contains several openings about its circumference. Other tip shapes include circular, duck bill and foraminous. The back end of the head connects to a fluid transporting conduit which is in the configuration of a hollow curved arm. The curved arm terminates and communicates with a hollow handle the terminal end of which is attached to tubing. This tubing allows the aspirated fluids to be removed from the operating field to a appropriate disposal container.

Most prior art yankauers are made by injection molding low melting point plastics. Using this fabrication technique it is not possible to produce a smooth curve or arc in the hollow curved arm. This curvature is usually achieved by making two post fabrication bends near the ends of the arm. This bending process materially increases the cost of manufacture. Most importantly, by making bends in the arm crimping occurs which reduces the interior diameter of the of the conduit and roughens interior surfaces at the bends. Both of these phenomena restrict fluid flow and increase the chance of fouling by debris in the body fluids such as bone chips collecting and impeding body fluid flow. If it were possible to more simply produce yankauers and at the same time eliminate the crimping problems described, an advance in the art would be afforded.

THE DRAWINGS

With respect to the drawings in which like parts have like numbers and of which:

THE INVENTION

The invention comprises an improved yankaner used to aspirate body fluids during surgical procedures. It comprises a hollow tip having at it's from end a body fluid receiving head. At it's back end is a body fluid delivery port sized to engage flexible tubing for transporting body fluids. A bore connects the receiving head with the delivery port.

The yankauer also consists of a curved arm having a channel extending throughout its length. One end of the curved arm is connected to the back end of the hollow tip and the other end is fitted to a handle which also contains substantially throughout its length a channel. This channel communicates with the channel located in the curved arm. Fitted into the channels of the curved arm and handle is flexible tubing the proximal end of which engages the delivery port in fluid sealing relationship.

Other features of the invention include as preferred embodiments that the radius of the curved arm is continuous and that the channels of the curved arm and the handle are troughs. The arc of curved arm, in a non-preferred embodiment, may not be completely continuous. Also, the proximal end of the tubing for transporting body fluids is luminally connected to the delivery port. That is to say that either the interior or the exterior of the proximal end of the tubing slides into or onto an opening or a lumen located in or on the delivery port.

To insure that the tubing is secured to the delivery port of the hollow tip it is desirable that the tubing be adhesively fastened thereto. Another feature of the invention is that the tubing be adhesively bonded to the channel of the curved arm when it is in the configuration of a trough. Alternatively, the channels in the curved arm and in the handle may be dimensioned to receive the tubing in a snug frictional engagement, thus eliminating the need for adhesive bonding. The channel in the handle may be configured to be a closed internal conduit even though the channel in the curved arm is a trough.

To allow visual observation of the body fluids being removed from a patient it is beneficial that the yankauer and the flexible tubing be fabricated from a clear plastics such as polystyrene or polyvinylchloride.

An important concept of the invention resides in the fact that since the yankauer is a carrier or support for the flexible tubing. The flexibility of the tubing provides a smooth passageway for the flow of body fluids therethrough even though the external radius of the tubing is not continuously arcuate. This feature prevents the unwanted hang-up of debris in the tubing thus making the entire device stoppage free during use.

DETAILED DESCRIPTION OF THE INVENTION

Figure 1:
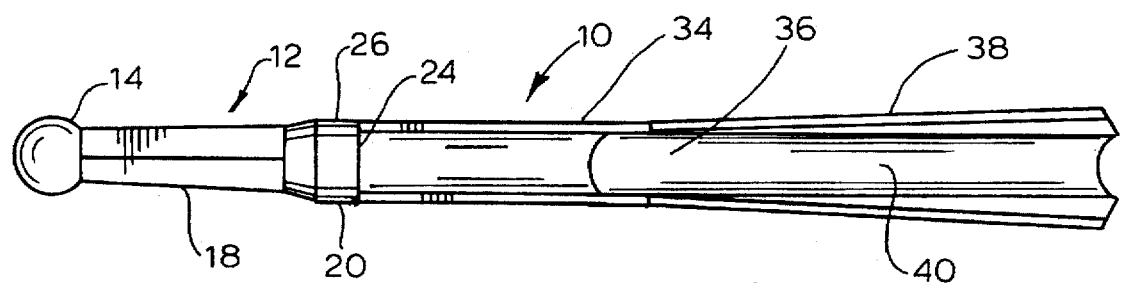
FIG. 1 is partial a top view of the yankauer of the invention illustrating the preferred open trough channel of the curved arm of the yankauer and the handle.
Figure 2:
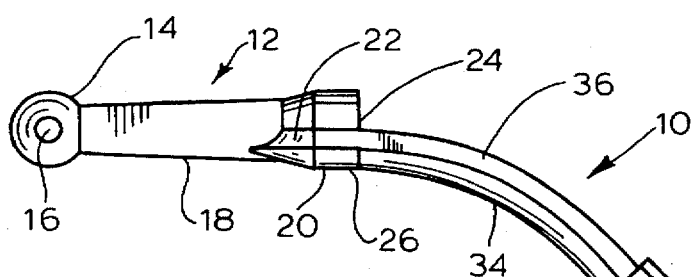
FIG. 2 is a full side view corresponding to FIG. 1
Figure 3:
FIG. 3 is a perspective view of a preferred ball shaped tip configuration.

With specific reference to the drawings there is shown a yankauer 10. The yankauer has at one end a hollow tip 12. The hollow tip has at it's terminal end a ball shaped head 14 for receiving body fluids. This is shown to best advantage in FIG. 3. It contains several openings 16 through which the body fluids to be aspirated enter. The ball shaped head 14 is fitted onto neck 18 which is shown in FIGS. 1, 2 and 3 as being rectangular in shape. It may be cylindrical in configuration or it may be eliminated so that the ball shaped head 14 directly connects to the delivery port 20. Neck 18 terminates and has as it's other end delivery port 20. Delivery port 20 is in fluid communication with the ball shaped head 14 via bore 22 which extends through the length of neck 18. The end 24 of the delivery port 20 is outwardly flared as indicated by the numeral 26. This flared opening may be considered as a lumen which is sized to receive in snug fitting relationship the proximal end 28 of flexible tubing 30. It is possible to change the configuration of the outward flare 26 of end 24 of delivery port 20 to an inwardly tapered lumen which would be sized to engage the interior opening 32 of flexible tubing 30, which feature is not shown in the drawings.

Figure 4:
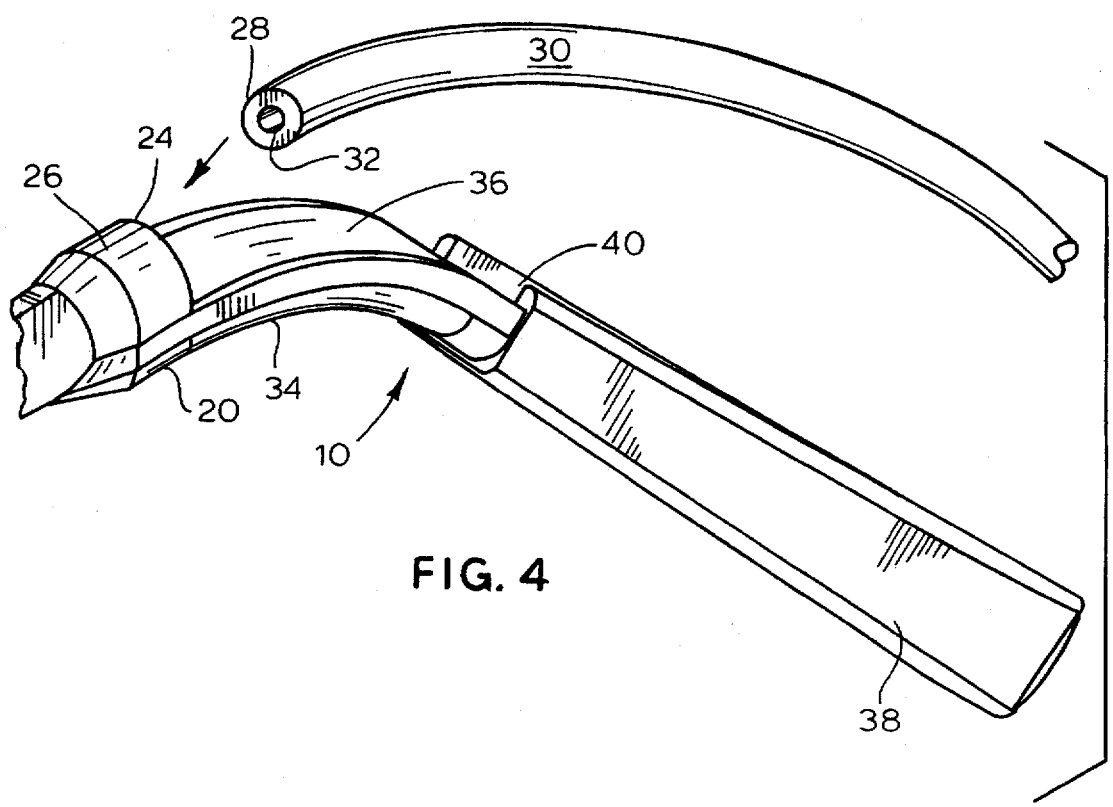
FIG. 4 is a perspective side view showing the relationship of the body fluid transporting flexible tubing to the yankauer.
Figure 5:
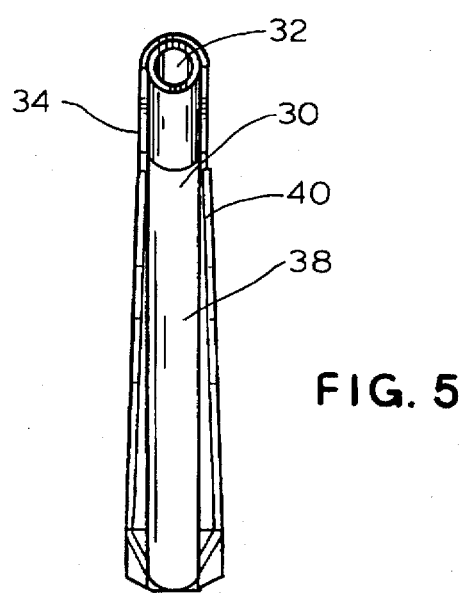
FIG. 5 is a partial vertical view.

Attached to delivery port 20 is curved arm 34 the curvature as shown in the drawings has a uniform radius which feature is not present in prior art yankauers. The curved arm contains substantially throughout its length channel 36. As shown dearly in FIG. 4 the channel 36 is in the form of an open trough, which represents a preferred embodiment of the invention. The channel 36 may be inclosed. Curved arm 34 terminates and connects to handle 38 which contains throughout its length channel 40 which communicates with channel 36 located in curved arm 34. The channel 40 is shown in the drawings as being trough shaped although it may be closed. If the handle 40 is closed then its terminal end 42 should contain an opening 44 dimensioned to slidably receive the flexible tubing 30.

By using the preferred embodiments of the invention it is possible to use quality molding plastics such as polystyrene which allows the curve in the curved arm 34 to be produced using injection molding technology. A further desirable feature of the invention is that the entire assembly may be constructed of clear plastics thus allowing visual observation of its performance during periods of use.

Proximal end 28 of flexible tubing 30 is desirably adhesively bonded to the outwardly flared end 26 of delivery port 24. To anchor the flexible tubing 30 to channel 36 of the curved arm 34 and channel 40 of handle 38 it is preferred that the tubing be adhesively attached to these channels.

As an alternative to adhesively bonding the flexible tubing 30 to channels 36 and 38, it is possible to anchor the flexible tubing by dimensioning these channels when they are troughs so that they are of slightly smaller diameter that the circumference of the flexible tubing 30. This allows flexible tubing 30 to be snap or be fitted into the channels which provides a snug tight anchored fit.

Since the flexible tubing has a uniform smooth bore bending it up to a much as 30-40 degrees does not impede flow of liquids therethrough. This, therefore, allows for the curved arm 34 to have an irregularly bend yet a uniform flow of fluid through the tubing may be maintained.

When the channels 36 and 40 in the curved arm 34 and handle 38 respectively are closed the yankauer is assembled by detaching the hollow tip 12 from the assembly or molding it as a separate component. The flexible tubing 30 is then attached the separate or detached hollow tip 12. Flexible tubing 301 is then threaded through the channels 36 and 40 of the curved arm 34 and the handle 38. Hollow tip 12 is then attached to the curved arm using known fastening means such as adhesive bonding. When this embodiment of the invention is practiced it is necessary that channels 38 and 40 be sufficiently generous in size so that flexible tubing 30 may be snaked therethrough.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

We claim:

1. An improved yankauer for aspirating body fluids during surgical procedures consisting of:
    a) a hollow tip having at it's front end a body fluid receiving head; and at it's back end a body fluid delivery port and a bore connecting the receiving head with the delivery port;
    b) a uniformly curved arm having a trough extending substantially throughout its length which curved arm has one end connected to the body fluid delivery port and the other end connected to;
    c) a handle containing substantially throughout its length a channel which communicates with the channel of the curved arm; and,
    d) a flexible tube disposed within the trough of the curved arm and the channel of the handle and with the proximal end of the flexible tube being connected to the body fluid delivery port.

2. The improved yankauer of claim 1 where the radius of the curved trough is continuous.

3. The improved yankauer of claim 1 where the end of the tube for transporting body fluids is luminally connected to the delivery port.

4. The improved yankauer of claim 3 where the end of the tube is adhesively bonded to the delivery port.

5. The improved yankauer of claim 1 where the tube is adhesively bonded to the curved trough.

6. The improved yankauer of claim 1 where the tube is friction fitted into the curved trough.

7. The improved yankauer of claim 1 where the channel in the handle is a trough.

8. The improved yankauer of claim 1 where the channel in the handle is an internal conduit.

9. The improved yankauer of claim 1 where the tube is a clear tubing.

10. The improved yankauer of claim 1 where the body fluid receiving head is in the shape of a ball.

* * * * *